United States Patent [19]

Branner-Jorgensen et al.

[11] Patent Number: 4,591,565

[45] Date of Patent: * May 27, 1986

[54] METHOD FOR THERMAL DESTABILIZATION OF MICROBIAL RENNET

[75] Inventors: Sven Branner-Jorgensen, Charlottenlund; Palle Schneider, Ballerup; Peter Eigtved, Copenhagen, all of Denmark

[73] Assignee: Novo Industri A/S, Denmark

[*] Notice: The portion of the term of this patent subsequent to Nov. 2, 1999 has been disclaimed.

[21] Appl. No.: 374,493

[22] Filed: May 3, 1982

Related U.S. Application Data

[63] Continuation of Ser. No. 138,460, Apr. 8, 1980, abandoned.

[30] Foreign Application Priority Data

Apr. 9, 1979 [DK] Denmark ............................ 79.1457

[51] Int. Cl.$^4$ .................. C12N 9/58; C12N 9/99; A23C 19/032
[52] U.S. Cl. ............................. 435/223; 426/36; 426/63; 435/184
[58] Field of Search ............... 426/36, 40, 63, 582; 435/223, 184

[56] References Cited

U.S. PATENT DOCUMENTS

4,348,482 9/1982 Cornelius ..................... 426/36 X
4,357,357 11/1982 Branner-Jorgensen et al. ..... 426/36

FOREIGN PATENT DOCUMENTS

2901542 11/1979 Fed. Rep. of Germany.

OTHER PUBLICATIONS

McBride-Warren, et al., Structural and Functional Determinants of *Mucor Miehei*, Protease, Biochimicz at Biophysicz Acta, vol. 328, 1973 (pp. 52–60).
The Condensed Chemical Dictionary, 8th ed. UNR Co., N.Y. 1971, (p. 668).
Concise Chemical and Technical Dictionary, Chem. Publi. Co., Inc., NY (1962), p. 709.

*Primary Examiner*—David M. Naff
*Attorney, Agent, or Firm*—Fidelman, Wolffe & Waldron

[57] ABSTRACT

Thermal stability of microbial rennet is reduced by treatment of the rennet in aqueous medium with aliphatic or inorganic peroxy acids or salts thereof. Preferably, the microbial rennet is *Mucor Miehei* rennet and the peroxy acid is a lower aliphatic peroxy acid such as peracetic acid. The thermally destabilized microbial rennet is inactivated when whey containing the rennet is pasteurized.

1 Claim, No Drawings

METHOD FOR THERMAL DESTABILIZATION OF MICROBIAL RENNET

This is a continuation of application Ser. No. 138,460, filed Apr. 8, 1980, now abandoned.

This invention relates to a method for thermal destabilization of microbial rennet. Rennet is a designation for a milk coagulating enzyme product.

In the production of cheese, the milk is coagulated in order to be able to separate the curds from the whey. Products containing rennin, which is a milk coagulating enzyme isolated from calf stomach, have long been used for this purpose. In the past, the demand for rennet could be met with calf rennet; but in recent years, several substitutes for calf rennet have been developed, including notably the microbial rennets from *Mucor miehei* and *Mucor pusillus*. *Mucor miehei* rennet is preferred by the cheese art for its low cost, its low unspecific proteolytic activity and its close resemblance to rennin concerning calcium ion sensitivity. The excellent storage stability of *Mucor miehei* rennet is another advantageous property which, at least partly, has been ascribed to its high thermal stability.

Some of the pasteurized whey is utilized as an additive to whole milk, e.g., in the form of a whey powder, to produce enriched milk, for instance as a baby food. The pasteurized whey resulting from cheese made with *Mucor miehei* rennet may still contain a minor level of rennet activity, due to the high thermal stability of the *Mucor miehei* rennet. Any residual rennet activity in the whey powder is undesirable, since protein coagulation is no longer wanted. Such could take place if the whey powder is used for the production of enriched milk as a baby food. The enriched milk may clot before it enters the stomach of the baby, e.g., in the feeding bottle, thereby causing an obstruction to flow of milk out of the bottle.

It is described in *Biochem. Biophys. Acta* 271 (1972) 93–101 (W. S. Rickert, Structural and Functional Determinants of *Mucor miehei* protease, I. Modification of the NH$_2$ terminus and lysine residues by carbamylation) that *Mucor miehei* protease (the active component of *Mucor miehei* rennet) can be carbamylated with potassium cyanate, and that the carbamylated product exhibits a minor degree of thermal destabilization. Practical experiments have shown that the thermal destabilization of the carbamylated enzyme is too small to solve the above-mentioned problem of rennet activity in pasteurized whey. Another approach is in Belgian patent application No. 6/47048 filed Dec. 24, 1979 which suggests acylating the enzyme for destabilizing purposes.

An approach related to practice of this invention has been to treat the microbial rennet with hydrogen peroxide, either as such or formed in situ. This approach is described in British patent application No. 2.024.828 A, published Jan. 16, 1980.

The object of this invention is to provide an economically feasible method for thermal destabilization of microbial rennet to such an extent that the disadvantages stemming from the residual microbial rennet activity in pasteurized whey are essentially overcome.

According to the invention it has been found that by using a specially selected category of peroxy compounds which exhibits a chemical character different from that of the peroxy compounds suggested in the previously cited British patent application it is possible to perform the thermal destabilization with a molar amount of peroxy compound in proportion to the total amount of protein present which is considerably lower than the corresponding amount of the hydrogen peroxide used in the previously cited British patent application.

Accordingly the first aspect of the invention comprises a method for reducing the thermal stability of microbial rennet by chemical modification thereof, which comprises treating the microbial rennet in an aqueous medium with a peroxy acid selected from the group consisting of inorganic peroxy acids and lower aliphatic peroxy acids, or salts thereof.

In the present specification and claims the term "lower aliphatic peroxy acid" designates a peroxy acid derivative of an aliphatic carboxylix acid having a straight or branched alkyl group containing not more than 6, and preferably not more than 4 carbon atoms.

As examples of lower aliphatic peroxy acids the following may be mentioned: peroxy formic acid, peroxy acetic acid, peroxy propionic acid, and peroxy butyric acid.

As examples of salts of inorganic peroxy acids the following may be mentioned: potassium peroxy sulphate and sodium peroxy phosphate.

Whereas the treatment in the previously cited British patent application is carried out by means of H$_2$O$_2$, either as such or formed in situ, it is assumed that the mechanism of the reaction performed according to this invention does not involve H$_2$O$_2$. Also it is assumed that this difference is the reason why it is possible according to the invention to obtain a satisfactory thermal destabilization by use of a molar amount of the peroxy compound in proportion to the total amount of protein present which is only a fraction, i.e. of the order of magnitude of around a tenth of the corresponding molar amount of H$_2$O$_2$ used in the previously cited British patent application.

The drastic reduction of the amount of reagent employed entails at least two advantages. In the first place the otherwise mandatory inactivation of excess reagent is obviated. Secondly, due to the fact that the microbial rennet is used in connection with goods for human consumption, contamination thereof by extraneous reagents should be kept at the lowest possible level.

It has been found that the microbial rennet modified according to the invention is significantly destabilized and that the degree of destabilization suffices to meet the requirements for whey utilization without having a highly detrimental effect on storage stability of the rennet preparation. Surprisingly it has been found that it is possible, according to the invention, to obtain a destabilization level (as defined hereinafter) of at least 8° C. preferably 10°–13° C. which, in the preferred range, makes the thermal stability of the modified enzyme correspond to that of calf rennet whereby the favorable properties of the calf rennet are combined with the favorable properties of the microbial rennet.

The rennet activity is measured according to British Standard 3624:1963 (Method for the determination of milk coagulating power of rennet).

Since this invention relates to a controlled thermal destabilization of microbial rennet, some elaboration is provided below on techniques to measure thermal stability and to quantify the reduction in thermal stability, i.e., the destabilization, this destabilization being expressed in °C.

Under ideal conditions, an enzyme may be denatured at a suitable (high) temperature level in such a way that the residual activity of the enzyme decreases as a function of time along an exponential decay curve, i.e., with a well-defined half life, the half life being a function of the temperature (°C.). The half life $T_{\frac{1}{2}}$ can be calculated according to the formula $$T_{\frac{1}{2}} = \frac{(t_2 - t_1) \ln 2}{\ln A_1 - \ln A_2}$$

where $A_1$ is the enzyme activity measured after heating to a specified temperature for the time $t_1$, where $A_2$ is the enzyme activity measured after heating to the same specified temperature for the time $t_2$. The half life will be shorter the higher the temperature, everything else being equal. For many enzymes, a change in the pH of the enzyme solution and the ion strength, and the presence of certain salts will influence the half life substantially. Furthermore, chemical derivatization of the enzyme can change the half life considerably. If a chemical derivatization of a particular enzyme causes thermal destabilization of the enzyme, the degree of destabilization is said to be N°C., if the original (non derivatized) enzyme and the derivatized enzyme have the same half life at N°C. and (N-n)°C. respectively.

It should be noted, however, that the destabilization values to a certain degree are approximate, due to the approximative character of the half life value. All destabilization values in this specification are measured at pH 6.0, since the results of the destabilization measurement are pH dependent.

Normally, the treatment according to the invention is accompanied by an activity loss. It has been found that, for economic reasons, the destabilization reaction should not be carried beyond the stage corresponding to a concommitant activity loss of around 50%, preferably of around 30%, more preferably less than 10%.

In a typical instance, the destabilization of about 10° or 11° C. with an activity loss limited to less than 10% seems to be an appropriate compromise between the above mentioned conflicting factors.

The peroxy acid should be used in such a concentration that the desired degree of destabilization is obtained in a resonable time, which may be anything from a few minutes up to 48 hours, or even a week. The ratio of peroxy acid to total protein in the enzyme product is important to the results. In case the concentration of the peroxy acid is too small the destabilization will be too small, and in case the concentration of the peroxy acid is too high the activity loss will be too high. The optimal concentrations ordinarily correspond to a molar proportion between the agent and the total amount of protein in the enzyme preparation of about 0.1 to 25 mmol of peroxy acid per g total protein. If the microbial rennet preparation is purified to a high unit activity level the quantity of peroxy acid may be reduced to as little as 0.05 mmol of peroxy acid per g of total protein.

The reaction temperature is not critical when the reaction temperatures are kept at levels, e.g., below about 30° C., where the stability of the enzyme is satisfactory. However, the stability of the enzyme should be enhanced by presence of known protein stabilizing agents, e.g., NaCl in an amount of 5–20% of the enzyme preparation, or sorbitol in the usual enzyme stabilizing amounts. The preferred reaction temperature range is 0°–30° C.

The destabilization level of at least 8° C., preferably 10° C. to 13° C., and the accompanying activity loss of no more than 30%, preferably less than 10%, are considered as limits on the practice of this invention.

A preferred embodiment of the method according to the invention comprises treating the microbial rennet with peroxy acetic acid or peroxy propionic acid.

Another preferred embodiment of the method according to the invention comprises treating the microbial rennet with monopersulphonic acid.

In another preferred embodiment of the method according to the invention the microbial rennet is *Mucor miehei* rennet.

In another preferred embodiment of the method according to the invention the treatment is carried out with a molar proportion in the reaction mixture between the peroxy acid and the total amount of protein in the enzyme preparation of between 0.1 and 25 mmol peroxy acid/g protein, preferably between 0.5 and 5 mmol peroxy acid/g protein.

In another preferred embodiment of the method according to the invention the aqueous medium has a pH value of between 2 and 9.

In another preferred embodiment of the method according to the invention the aqueous medium has a temperature of between 0° and 30° C.

The second aspect of the invention comprises the destabilized micribial rennet, whenever prepared by means of the method according to the invention.

The third aspect of the invention comprises a method for cheese-making wherein the modified rennet according to the invention is used for milk coagulation.

In practice, it has been discovered that the employment of thermally destabilized rennet is preferred for making long-hold cheeses.

The destabilization process may be, and preferably is, carried out as the final step in the preparation of the microbial rennet. In fact, (commercially) pure microbial rennet or rennet concentrate may be employed in practice of this invention. Thus, for example, the pH of a stabilized microbial rennet solution otherwise ready for the usual finishing operations prior to delivery is adjusted to the predetermined treatment level (e.g., pH 5) and then admixed with stirring at ambient temperature with a solution of the peroxy acid, the amount of peroxy acid being in the aforementioned molar proportion range of total protein in the microbial rennet solution. The mixture is then left to react until the desired destabilization level is attained, e.g. for 4 hours. The thermally destabilized enzyme product may be subjected to the usual finishing operations, e.g., filtration, adjustment of pH and unit enzyme activity to standardized levels, etc.

The invention will now be described in more detail by reference to the following examples.

The starting material in the following examples is a rennet concentrate prepared as indicated in "2. Pilot plant experiment" in British Pat. No. 1,108,287, only the culture liquid was concentrated to an activity approximately corresponding to a 1% solution of the pure enzyme (Comptes Rendus des Travaux du Laboratorie Carlsberg, (1970) Vol. 37, No. 14, 301–325). For the sake of brevity, this concentrate will be referred to in the following as "RENNILASE 46". The activity of the concentrate is approximately 50,000 Rennet units per ml (or 50,000 S units/ml).

EXAMPLE 1

5 ml of Rennilase 46 is diluted to 15 ml during addition of NaCl until a concentration of 12% in the mixture. Then 50 μl of 37% peroxy acetic acid (containing 3.8% $H_2O_2$) is added, whereby simultaneously the pH value is adjusted to 2.5 with 4N HCl. After a reaction time of 1 hour at 25° C. the mixture is neutralized to pH 7.0 with 4N NaOH. The activity yield is around 20%, and the half life at 55° C. at the earlier mentioned conditions is below 5 minutes, corresponding to a destabilization of at least 13° C.

EXAMPLE 2

150 ml of Rennilase 46 was diluted with 150 ml of water and divided into three 100 ml portions, the pH values of which were adjusted to 3, 5, and 7 respectively. At ambient temperature and under vigorous agitation 300 μl of a commercial 25% peroxy acetic acid (1 mmol) was added to each of the three portions, and the pH was simultaneously readjusted by addition of 4N NaOH. The samples were stored overnight at 4° C. before they were analyzed. The experiment was repeated, but this time the dosage of peroxy acetic acid was reduced to 0.5 mol by the addition of 750 μl. of a 5% peroxy acetic acid solution.

The results appear from the following table.

| pH | Dosage mmol peroxy acetic acid | Activity yield % | Half life at 55° C., pH 6.0, minutes | Destabilization °C. |
|---|---|---|---|---|
| 3 | 0.5 | 105 | 4.9 | 13 |
| 5 | 0.5 | 106 | 5.6 | 13 |
| 7 | 0.5 | 84 | 7.4 | 12 |
| 3 | 1 | 86 | 3.0 | 14 |
| 5 | 1 | 103 | 3.0 | 14 |
| 7 | 1 | 84 | 3.7 | 14 |

EXAMPLE 3

150 ml of Rennilase 46 was diluted with 150 ml of water and divided into three 100 ml portions the pH values of which were adjusted to 3, 5, and 7, respectively. At ambient temperature and under agitation of 1 ml 1M potassium monopersulphate was added to each of the three portions, and the pH was readjusted. The samples were stored overnight at 4° C. before they were analyzed.

The experiment was repeated, but this time there was added 2 ml of the 1M potassium monopersulphate solution to each portion.

The results appear from the following table.

| pH | Dosage mmol KHSO$_5$ | Activity yield % | at 55°, pH 6.0, minutes | Destabilization °C. |
|---|---|---|---|---|
| 3 | 1 | 105 | 53 | 8 |
| 5 | 1 | 112 | 58 | 8 |
| 7 | 1 | 103 | 41 | 8 |
| 3 | 2 | 102 | 32 | 9 |
| 5 | 2 | 106 | 30 | 9 |
| 7 | 2 | 97 | 16 | 10 |

EXAMPLE 4

Six portions of 50 ml Rennilase 46 were diluted with 50 ml water, and the pH value was adjusted to 5. 75, 150, 300, 450, 600, and 750 μl, respectively, of a 5% peracetic acid (with 0,6% $H_2O_2$) were added to the above indicated six portions under vigorous stirring, and simultaneously the pH value was readjusted to 5 with 4N NaOH. After 1 hour at room temperature 1 ml samples were withdrawn for analysis. The results are shown in the following table.

| Dosage peracetic acid mmole | Yield % | Half life at 55° C., pH 6.0 minutes | Destabilization °C. |
|---|---|---|---|
| 0.05 | 104 | 1045 | 1 |
| 0.1 | 106 | 313 | 4 |
| 0.2 | 105 | 45 | 8 |
| 0.3 | 106 | 14 | 11 |
| 0.4 | 102 | 8 | 12 |
| 0.5 | 102 | 6 | 13 |

EXAMPLE 5

Three portions of 50 ml Rennilase 46 were diluted with 50 ml water, and the pH value was adjusted to 5. To one portion was added 0.55 ml, and to the second portion was added 1.10 ml of an approx. 0.46M performic acid (0.1M $H_2O_2$) under vigorous stirring and simultanious adjustment of pH to 5 with 4N NaOH. To the third portion was added 2,2 ml of an approx. 0.45M performic acid which has been neutralized with cold 4N NaOH.

After 2½ hours at room temperature 1 ml samples were withdrawn for analysis.

The results are shown in the following table.

| Dosage performic acid mmole | Yield % | Half life at 55° C., pH 6.0 minutes | Destabilization °C. |
|---|---|---|---|
| 0.25 (acidic) | 86 | 8.8 | 12 |
| 0.5 (acidic) | 70 | 3.4 | 14 |
| 1.0 (neutral) | 97 | 6 | 13 |

EXAMPLE 6

Two portions of 50 ml Rennilase 46 were diluted with 50 ml water, and the pH value was adjusted to 5. To one portion was added 5 ml of an approx. 0.2M perpropionic acid (0.1M $H_2O_2$) with simultaneous pH adjustment with 4N NaOH. To the second portion was added 5 ml of the approx. 0.2M perpropionic acid which has been neutralized beforehand.

The experiment was repeated, only 5 ml portions of an approx. 0.2M perbutyric acid (0.1M $H_1O_2$) were used as the reagent.

After 2 hours at room temperataure 1 ml samples were withdrawn for analysis.

The results appear from the following table.

| Reagent | Dosage mmole approx. | Yield % | T$_½$ at 55° C., 6.0 minutes | Destabilization °C. |
|---|---|---|---|---|
| perpropionic acid | 1 | 88 | <3 | >14 |
| perpropionic acid neutral | 1 | 106 | <3 | >14 |
| perbutyric acid | 1 | 82 | <3 | >14 |
| perbutyric acid neutral | 1 | 102 | <3 | >14 |

We claim:
1. A method for producing microbial rennet having reduced thermal stability in cheese making comprising reacting *Mucor Miehei* microbial rennet in an aqueous medium with effective amounts of a modifying agent selected from the group consisting of peracetic acid and salts thereof to produce a microbial rennet which has reduced thermal stability by at least 8° C. and which retains no less than 70% of its milk coagulating activity.

* * * * *